United States Patent [19]

Endicott, Jr. et al.

[11] 4,137,255

[45] Jan. 30, 1979

[54] PROCESS FOR SEPARATION OF NITROGLYCERIN FROM MIXTURES WITH DIETHYLENE GLYCOL

[75] Inventors: David W. Endicott, Jr., Brigham City; Charles L. Denton, North Ogden; Michael L. Levinthal, Brigham City, all of Utah

[73] Assignee: Thiokol Corporation, Newtown, Pa.

[21] Appl. No.: 870,773

[22] Filed: Jan. 19, 1978

[51] Int. Cl.$^2$ ............................................. C07C 77/02
[52] U.S. Cl. ..................................... 260/467; 149/101
[58] Field of Search ........................ 149/101; 260/467

[56] References Cited

U.S. PATENT DOCUMENTS 4,047,989  9/1977  Ostern .............................. 149/101 X

FOREIGN PATENT DOCUMENTS 734501  5/1966  Canada ................................... 260/467

*Primary Examiner*—Leland A. Sebastian
*Attorney, Agent, or Firm*—Stanley A. Marcus; Royal E. Bright

[57] ABSTRACT

A process for the separation of nitroglycerin from mixtures of nitroglycerin and diethylene glycol diluent which avoids the presence of undiluted nitroglycerin is disclosed. The process avoids the hazards inherent in handling undiluted nitroglycerin.

1 Claim, No Drawings

PROCESS FOR SEPARATION OF NITROGLYCERIN FROM MIXTURES WITH DIETHYLENE GLYCOL

The government has rights to this invention pursuant to Contract N0003074C0100, awarded by the U.S. Navy.

BACKGROUND OF THE INVENTION

The present invention relates to the art of handling and transporting sensitive liquid explosives, specifically nitroglycerin.

It is a well-known fact that nitroglycerin is an unstable liquid which in the absence of stabilizing ingredients is subject to detonation from shock and other initiating events. Among the many known stabilizing materials which may be added to nitroglycerin for added safety and convenience in handling and shipping is relatively non-volatile diethylene glycol. Non-volatility is a desirable attribute because if the container for the mixture of nitroglycerin and stabilizer should be imperfectly sealed a volatile stabilizer such as acetone may evaporate leaving neat nitroglycerin in the container, an undesirable occurrence.

In formulating explosives and other pyrotechnic devices from nitroglycerin it is normally necessary to separate the diethylene glycol. This is now done by a simple water extraction of the mixture which results in removal of diethylene glycol to the aqueous phase leaving neat or undiluted nitroglycerin as a residue. The handling of this residue then requires the extreme care which must be afforded neat nitroglycerin.

The present invention provides a method for separating diethylene glycol from mixtures with nitroglycerin while avoiding the formation of neat nitroglycerin.

Applicants are unaware of any prior art which is materially relevant to this invention.

SUMMARY OF THE INVENTION

The invention provides in a process aspect a process for the separation of nitroglycerin from mixtures of nitroglycerin and diethylene glycol without permitting the formation of undiluted nitroglycerin which comprises:
  (a) treating a mixture of nitroglycerin and diethylene glycol with an equal weight of methylene chloride to form a homogeneous solution of the three materials;
  (b) treating the solution of step a with an equal volume of water to form a two phase system;
  (c) separating and recovering the heavier organic phase of the two phase system of step b from the lighter aqueous phase of said two phase system; and
  (d) repeating the aqueous partitioning of the organic phase of step c as in steps b and c until said organic phase contains up to the minimum acceptable content of diethylene glycol.

The tangible embodiment produced by this process aspect possesses the inherent physical properties of being a homogeneous liquid, substantially immiscible with water and substantially less sensitive to initiation of decomposition than neat or undiluted nitroglycerin.

The tangible embodiment produced by this process aspect of the invention possesses the inherent applied use characteristic of being a relatively stable solution of nitroglycerin in a relatively volatile solvent which is readily evaporated from formulated propellant binders, explosives or other pyrotechnics prepared therefrom.

DESCRIPTION OF THE PREFERRED EMBODIMENT

The manner of practicing the invention will now be illustrated with reference to a specific embodiment thereof so as to enable one skilled in the art to practice the same as follows:

Nitroglycerin containing about 30% diethylene glycol as normally stabilized for shipping may be treated in a suitable container with a quantity of methylene chloride approximately equal in weight to that of the nitroglycerin diethylene glycol mixture. A quantity of water equal in volume to that of the previously formed mixture of nitroglycerin, diethylene glycol and methylene chloride may then be added. This mixture may then be thoroughly agitated for a short period of time, conveniently about five minutes, after which the heavier organic phase may be separated from the lighter aqueous phase. The heavier organic phase may be partitioned with water a number of additional times until analysis of the organic phase, conveniently by gas chromatography, indicates substantial absence of or the minimum acceptable level of diethylene glycol. At this point the organic phase may then be used for processing into the desired formulation.

One skilled in the art will recognize that the aqueous phases recovered from the partitioning process aforedescribed will contain some quantities of nitroglycerin and that, while not being essential to the basic operation of the invention, due care should be observed in their disposal.

One skilled in the art will also recognize that the use of methylene chloride as a replacement diluent involves the use of a relatively volatile non-flammable solvent thus introducing an additional safety factor. It will also be recognized that methylene chloride will frequently be an aid in processing the various pyrotechnic formulations in that it forms an azeotrope (98.5% $CH_2Cl_2$, 1.5% $H_2O$) and on evaporation from a formulation may assist in further drying thereof.

As used herein and in the appended claims the term "minimum acceptable level of diethylene glycol" means that amount of diethylene glycol which may conveniently be allowed to remain in the nitroglycerin while not adversely affecting formulation, stability or operation of the finished explosive or pyrotechnic device. Such levels are already known or readily determinable in simple empirical fashion by a skilled journeyman in the art.

The following example further illustrates the best mode contemplated by the inventors for the practice of their invention.

To a mixture of nitroglycerin (70%) and diethylene glycol (30%) (20 Kg) is added an equal weight of methylene chloride. The total volume of the mixture is about 55 l. This mixture is then partitioned with an equal volume of water four times by stirring for about 5 minutes after the addition of each portion of water and then separating and discarding to explosive disposal the lighter aqueous phase. After the fourth partitioning no diethylene glycol could be detected in the organic phase by gas chromatography.

The organic phase consisting of nitroglycerin, methylene chloride and a trace of water was then used without further treatment to prepare a standard double base propellant binder premix, during the sparging of which the methylene chloride was removed by evaporation.

The subject matter which Applicants regard as their invention is particularly pointed out and distinctly claimed as follows:

1. A process for the separation of nitroglycerin from mixtures of diethylene glycol and nitroglycerin without the formation of undiluted nitroglycerin which comprises:
   (a) treating a mixture of nitroglycerin and diethylene glycol with an equal weight of methylene chloride to form a homogeneous solution of the three components;
   (b) treating the solution of step a with an equal volume of water to form a two phase system;
   (c) separating and recovering the heavier organic phase of the two phase system of step b from the lighter aqueous phase of said two phase system; and
   (d) repeating the aqueous partitioning of the organic phase of step c as in steps b and c until said organic phase contains up to the minimum acceptable quantity of diethylene glycol.

* * * * *